US012636182B2

(12) United States Patent
Drane

(10) Patent No.: US 12,636,182 B2
(45) Date of Patent: May 26, 2026

(54) PALM COOLING ASSEMBLY

(71) Applicant: Christopher Drane, New Bedford, MA (US)

(72) Inventor: Christopher Drane, New Bedford, MA (US)

( * ) Notice: Subject to any disclaimer, the term of this patent is extended or adjusted under 35 U.S.C. 154(b) by 406 days.

(21) Appl. No.: 18/381,257

(22) Filed: Oct. 18, 2023

(65) Prior Publication Data

US 2025/0127651 A1     Apr. 24, 2025

(51) Int. Cl.
    *A61F 7/00*          (2006.01)
(52) U.S. Cl.
    CPC ........ *A61F 7/00* (2013.01); *A61F 2007/0036* (2013.01)
(58) Field of Classification Search
    CPC . G06F 3/0325; G06F 3/0346; G08C 2201/32; A61F 2007/0036; A61F 2007/0078; A61F 7/00
    See application file for complete search history.

(56) References Cited

U.S. PATENT DOCUMENTS 5,127,395 A     7/1992  Bontemps
9,089,176 B1    7/2015  Crowder 9,151,527 B2    10/2015  Boarman
D914,773 S       3/2021  Benlolo
11,622,910 B2    4/2023  Newns
2005/0028245 A1  2/2005  Chiba
2014/0165598 A1*  6/2014  Boarman ................. F25C 1/22
                                                    62/347
2014/0358204 A1  12/2014  Dickie
2020/0107596 A1   4/2020  Caruso
2021/0318049 A1* 10/2021  Moczygemba ........... F25C 5/08

FOREIGN PATENT DOCUMENTS

CA          2020289        6/1991

* cited by examiner

*Primary Examiner* — Tigist S Demie

(57)                    ABSTRACT

A palm cooling assembly for cooling a device used to lower a body temperature of a user includes a housing having a base wall and a peripheral wall. The peripheral wall is attached to and extends upwardly from the base wall defining an interior area. The peripheral wall has an upper edge defining an opening into the interior area. A panel is coupled to the upper edge and extends across the opening to enclose the interior area. The panel has a well therein. A palm cooling object is removably positionable in the well. The palm cooling object has a shape that is configured to at least partially cover a palm of a hand of a user who is gripping the palm cooling object. A refrigeration system controls a temperature of the interior area whereby the palm cooling object is cooled to the temperature when positioned in the well.

19 Claims, 5 Drawing Sheets

PALM COOLING ASSEMBLY

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION

(1) Field of the Invention

The disclosure relates to body temperature regulation devices and more particularly pertains to a new body temperature regulation device for cooling a device used to lower a body temperature of a user.

(2) Description of Related Art Including Information Disclosed Under 37 CFR 1.97 and 1.98

The prior art relates to body temperature regulation devices. In particular, the prior art relates to devices and methods for lowering a body temperature of a user. Such devices are used to address heat-related illnesses, for example when the user is exposed to high ambient temperatures. Such devices may also be used to address other conditions, such as heat flashes. Lowering the body temperature can also be an important recovery technique when a user is exercising. For example, some athletes will use an ice bath to drastically lower their body temperature after a strenuous workout to aid recovery and reduce muscle soreness. Another popular technique is palm cooling, which involves cooling the palms of the user during breaks between strenuous physical activity. The goal of palm cooling is to moderate increases in core temperature that can result from physical activity. Reducing core temperature can help improve blood circulation, lower heart rate, boost physical endurance, and decrease water loss. Typically, palm cooling is done with ice cubes or by placing the hands into cold water during exercise breaks. There is a need in the art for a portable, convenient device that can be used for palm cooling without requiring access to cold water or ice cubes.

BRIEF SUMMARY OF THE INVENTION

An embodiment of the disclosure meets the needs presented above by generally comprising a housing having a base wall and a peripheral wall. The peripheral wall is attached to and extends upwardly from the base wall defining an interior area. The peripheral wall has an upper edge defining an opening into the interior area. A panel is coupled to the upper edge and extends across the opening to enclose the interior area. The panel has a well therein. A lid is positionable on the housing and abuts the upper edge to selectively cover the panel. A palm cooling object is removably positionable in the well. The palm cooling object is configured for gripping by a hand of a user. The palm cooling object has a shape that is configured to at least partially cover a palm of the hand. A refrigeration system is positioned in the interior area. The refrigeration system is configured to control a temperature of the interior area below the panel whereby the palm cooling object is cooled to the temperature when the palm cooling object is positioned in the well.

There has thus been outlined, rather broadly, the more important features of the disclosure in order that the detailed description thereof that follows may be better understood, and in order that the present contribution to the art may be better appreciated. There are additional features of the disclosure that will be described hereinafter, and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein.

DETAILED DESCRIPTION OF THE INVENTION

Figure 1:
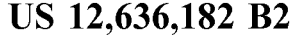
FIG. 1 is a top front isometric view of a palm cooling assembly according to an embodiment of the disclosure.
Figure 2:
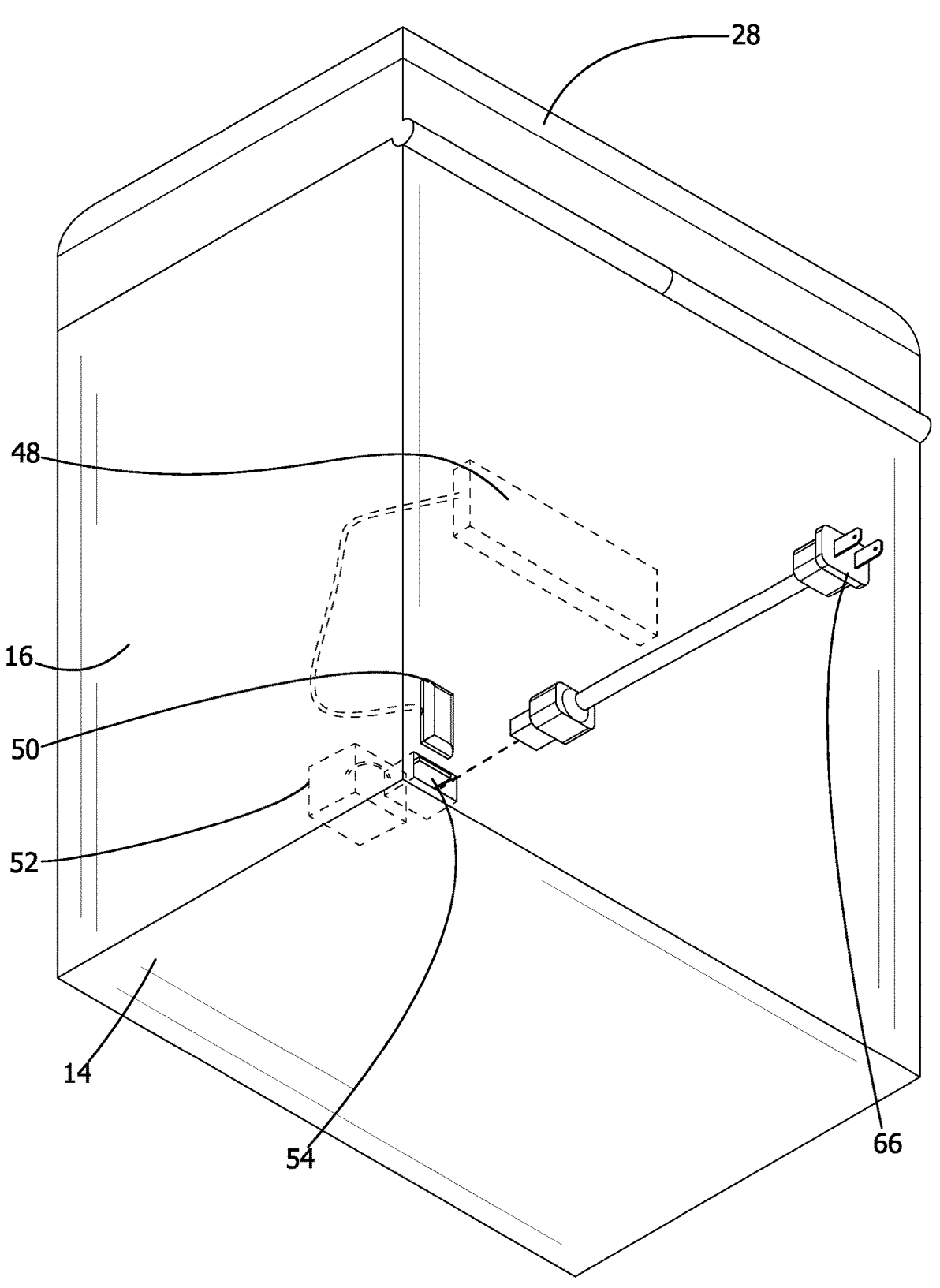
FIG. 2 is a bottom rear isometric view of an embodiment of the disclosure.
Figure 3:
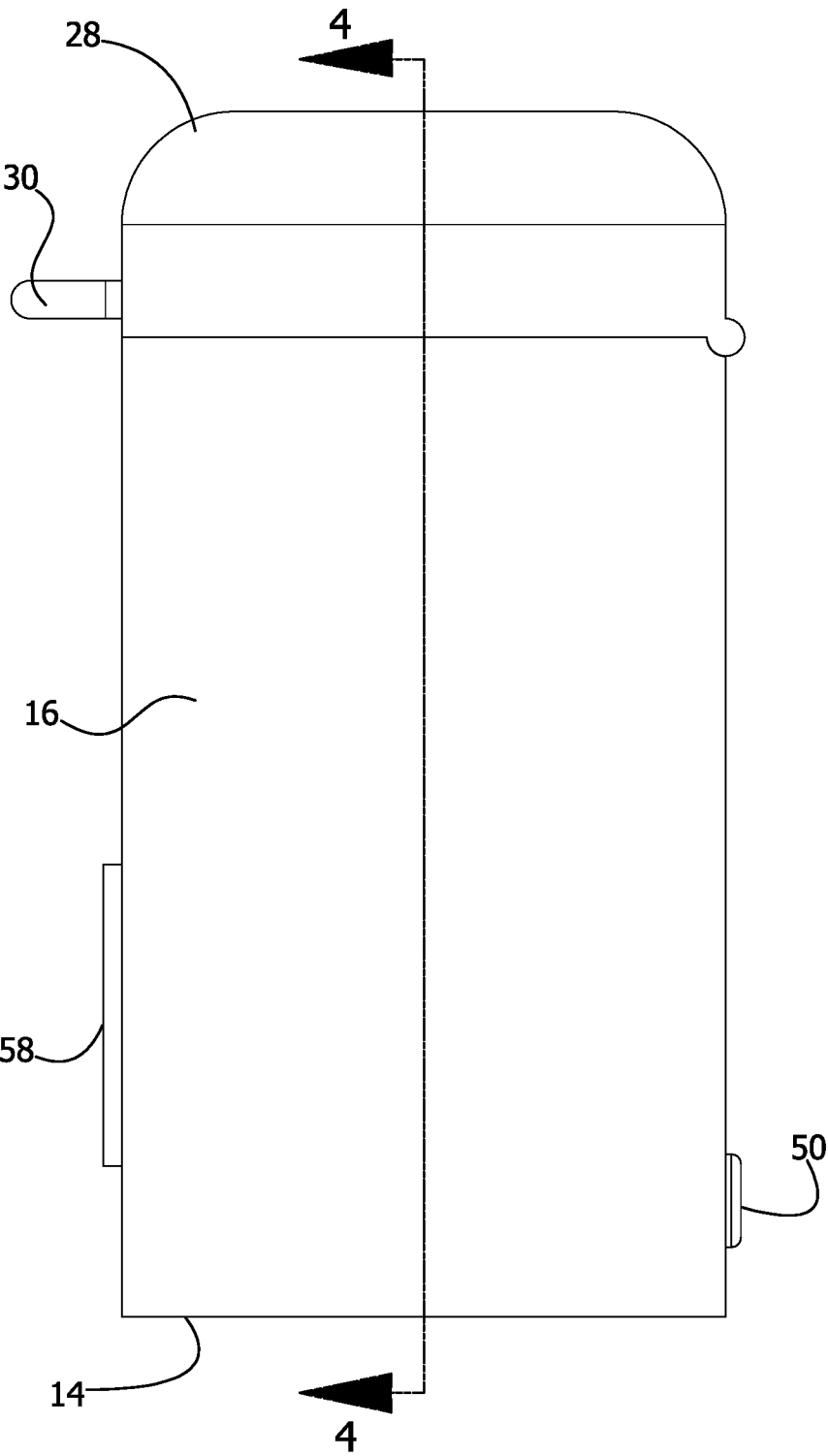
FIG. 3 is a side view of an embodiment of the disclosure.
Figure 4:
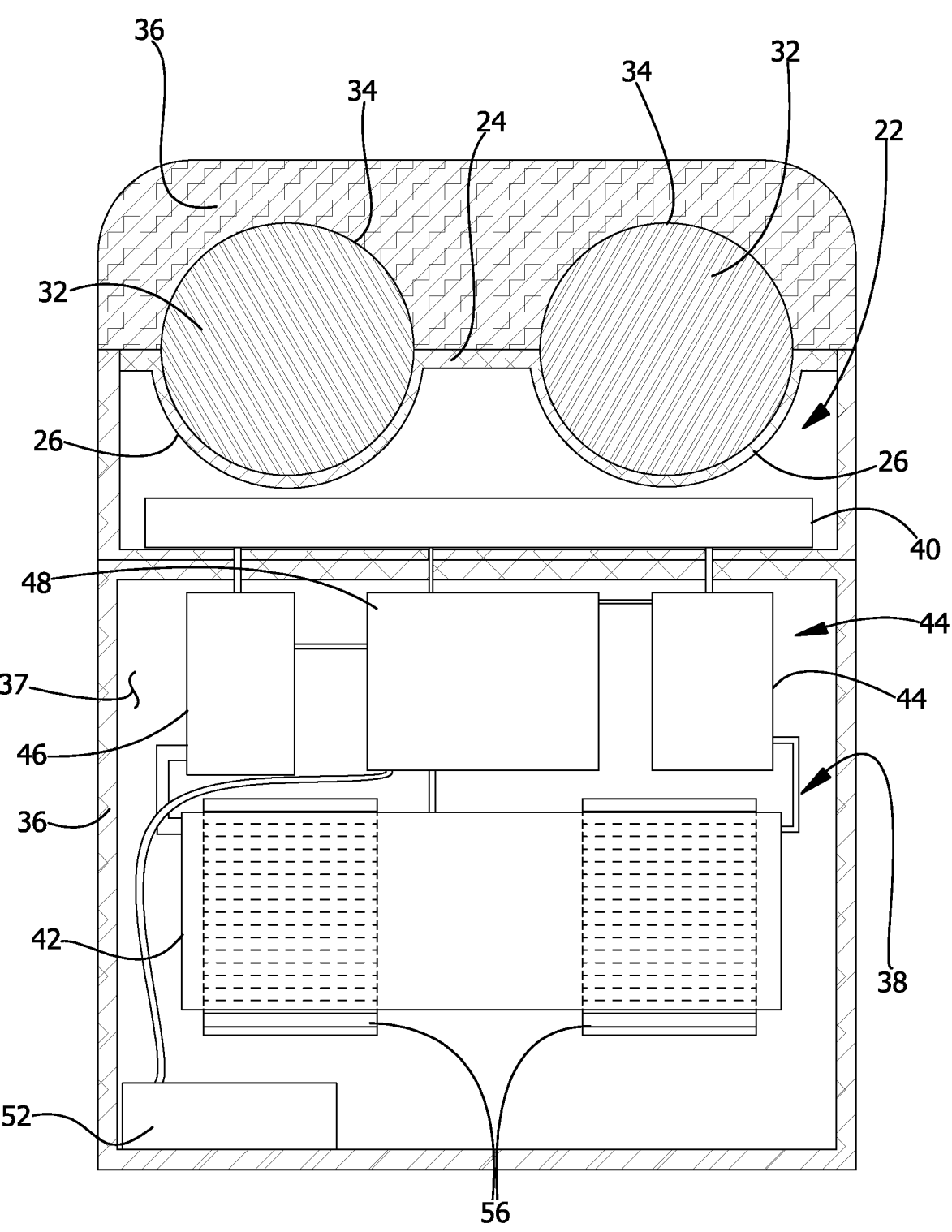
FIG. 4 is a cross-sectional view of an embodiment of the disclosure.
Figure 5:
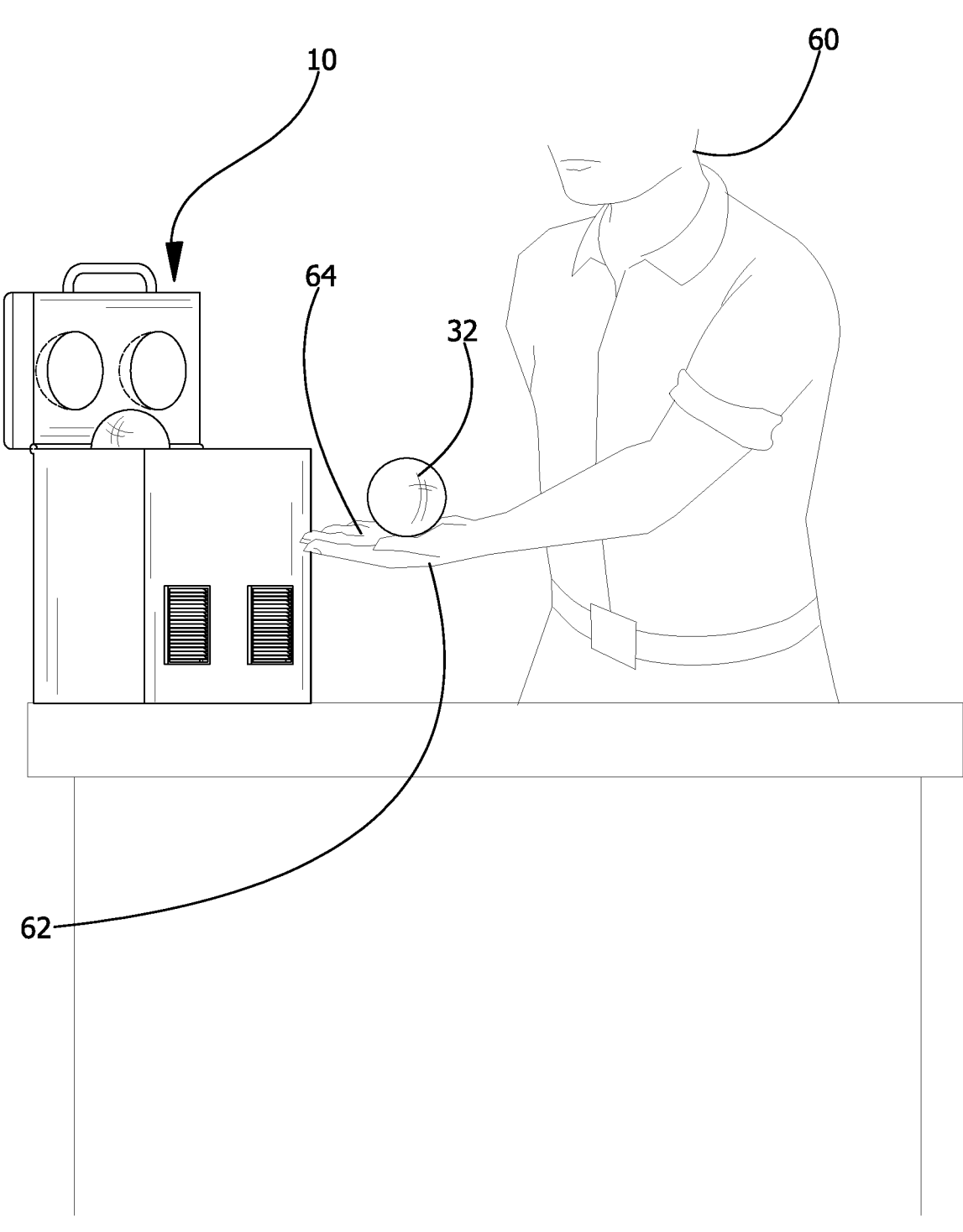
FIG. 5 is an in-use view of an embodiment of the disclosure.

With reference now to the drawings, and in particular to FIGS. 1 through 5 thereof, a new body temperature regulation device embodying the principles and concepts of an embodiment of the disclosure and generally designated by the reference numeral 10 will be described.

As best illustrated in FIGS. 1 through 5, the palm cooling assembly 10 generally comprises a housing 12 having a base wall 14 and a peripheral wall 16. The peripheral wall 16 is attached to and extends upwardly from the base wall 14 defining an interior area 18. The peripheral wall 16 has an upper edge 20 defining an opening 22 into the interior area.

A panel 24 is coupled to the upper edge 20 and extends across the opening 22 whereby the panel 24 encloses the interior area 18. The panel 24 may comprise a thermally conductive material. The panel 24 has a well 26 therein.

A lid 28 is positionable on the housing 12 and abuts the upper edge 20 to selectively cover the panel 24. The lid 28 may be pivotably coupled to the peripheral wall 16. A handle 30 may be coupled to the lid 28 for positioning the lid 28 on the housing 12 to cover the panel 24. An insulation material 36 may cover an interior surface 37 of the housing 12 and the lid 28.

A palm cooling object 32 is removably positionable in the well. The palm cooling object 32 is generally configured to inhibit conduction of heat away from the palm cooling object. For example, the palm cooling object 32 may comprise a stainless-steel material. The palm cooling object 32 is configured for gripping by a hand 62 of a user 60 and generally has a shape that is configured to at least partially cover a palm 64 of the hand 62. In some embodiments, the panel 24 may have two wells 26 configured to receive two palm cooling objects 32, for example so that the user 60 can hold one palm cooling object 32 in each hand 62.

The lid 28 may have a cavity 34 therein. Each of the well 26 and the cavity 34 may have a shape that is complementary to the shape of the palm cooling object 32. The well 26 may partially cover the palm cooling object 32 when the palm cooling object 32 is positioned in the well 26 and the cavity 34 may partially cover the palm cooling object 32 when the lid 28 is covering the panel 24.

The embodiments shown depict the palm cooling object 32 having a spherical shape. However, the palm cooling object 32 may comprise any shape. For example, rather than being spherical, the palm cooling object 32 could have a cube shape, a cylindrical shape, a prismatic shape, a hexagonal or pentagonal shape, or any other shape. The well 26 and cavity 34 may have a shape that is complementary to whatever shape the palm cooling object 32 comprises.

A refrigeration system 38 is positioned in the interior area 18. The refrigeration system 38 is configured to control a temperature of the interior area 18 whereby the palm cooling object 32 is cooled to the temperature when the palm cooling object 32 is positioned in the well 26. For example, the temperature may be between 30.0° Fahrenheit and 60.0° Fahrenheit. The refrigeration system 38 generally includes an evaporator 40, a condenser 42, a compressor 44, and an expansion device 46.

The evaporator 40 may be positioned proximate to the panel 24 within the interior area 18. The evaporator 40 absorbs heat from the palm cooling object 32 when the palm cooling object 32 is positioned in the well 26. The evaporator 40 is configured to heat a refrigerant whereby a phase of the refrigerant changes from a liquid to a vapor.

The condenser 42 may also be positioned within the interior area 18. Generally, the condenser 42 is spaced from the evaporator 40. The condenser 42 is configured to cool the refrigerant whereby the phase of the refrigerant changes from the vapor to the liquid.

The compressor 44 is fluidly coupled to the evaporator 40 and to the condenser 42. The compressor 44 is configured to increase a pressure of the refrigerant as the refrigerant moves through the compressor from the evaporator 40 to the condenser 42.

The expansion device 46 is fluidly coupled to the evaporator 40 and to the condenser 42. The expansion device 46 is configured to reduce the pressure of the refrigerant as the refrigerant moves through the expansion device 46 from the condenser 42 to the evaporator 40.

A central processing unit 48 may be positioned in the interior area 18. The central processing unit 48 is operationally or electronically coupled with the refrigeration system 38. For example, the central processing unit may be electronically coupled to the refrigeration system 38 with a hardwired connection. The central processing unit 48 actuates the refrigeration system 38 to control the temperature.

A switch 50 may be coupled to the housing 12, for example being positioned on the peripheral wall 16. The switch 50 is operationally or electronically coupled with the central processing unit 48. For example, the switch 50 may be operationally coupled with the central processing unit 48 by being in wireless communication with the central processing unit 48. The switch 50 is actuatable to selectively turn the central processing unit 38 off and on whereby the central processing unit 48 actuates the refrigeration system 38 to control the temperature of the interior area 18.

A power source 52 may be electronically coupled with the central processing unit 48. For example, the power source 52 may be a rechargeable battery. A charging port 54 may be positioned inset into the peripheral wall 16 and may be exposed on the peripheral wall 16. The charging port 54 may be electronically coupled to the power source 52 and configured to receive a charging cord 66.

The peripheral wall 16 may have a vent 56 extending therethrough. The vent 56 is generally configured to discharge heat from the interior area 18. For example, the heat may be generated by the power source 52, the condenser 42, or the ambient temperatures surrounding the palm cooling assembly 10. The vent 56 may be positioned proximate to the power source 52 and the condenser 42 to more effectively remove the heat generated by those components. A grill 58 may be coupled to the peripheral wall 16 to cover the vent 56.

In use, the user 60 can remove the palm cooling object 32 from the well 26 after opening the lid 28. The user 60 can hold the palm cooling object 32 in their palm 64 to reduce their core body temperature. To cool the palm cooling object 32, the user can position the palm cooling object 32 in the well 26 and close the lid 28. The user 60 can then actuate the refrigeration system 38, for example using the switch 50 that is operationally coupled to the central processing unit 48 controlling the refrigeration system 38. The refrigeration system 38 will refrigerate, or remove heat from, the interior area 38 below the panel 24. The refrigeration system 38 will thereby cool the palm cooling object 32 for later use.

In some embodiments, the palm cooling assembly 10 is small and portable. For example, the palm cooling object 32 may be a sphere shape having a diameter between 1.0 inch and 3.0 inches. In such embodiments, the housing may have a length between 5.0 inches and 7.0 inches, a width between 7.0 inches and 9.0 inches, and a height between 3.0 inches and 5.0 inches. In other embodiments, the palm cooling assembly 10 may be smaller, for increased portability, or larger, for increased cooling capability.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. A palm cooling assembly comprising:

a housing having a base wall and a peripheral wall, the peripheral wall being attached to and extending upwardly from the base wall defining an interior area, the peripheral wall having an upper edge defining an opening into the interior area;

a panel being coupled to the upper edge and extending across the opening whereby the panel encloses the interior area, the panel having a well therein;

a lid being positionable on the housing and abutting the upper edge to selectively cover the panel;

a palm cooling object being removably positionable in the well, the palm cooling object being configured for gripping by a hand of a user, the palm cooling object having a shape being configured to at least partially cover a palm of the hand; and a refrigeration system being positioned in the interior area, the refrigeration system being configured to control a temperature of the interior area whereby the palm cooling object is cooled to the temperature when the palm cooling object is positioned in the well.

2. The palm cooling assembly of claim 1, the panel further comprising a thermally conductive material.

3. The palm cooling assembly of claim 1, wherein the palm cooling object is configured to inhibit conduction of heat away from the palm cooling object.

4. The palm cooling assembly of claim 1, the palm cooling object further comprising a stainless-steel material.

5. The palm cooling assembly of claim 1, further comprising a handle being coupled to the lid.

6. The palm cooling assembly of claim 1, wherein the lid has a cavity therein, each of the well and the cavity having a shape being complementary to the shape of the palm cooling object, wherein the well partially covers the palm cooling object when the palm cooling object is positioned in the well and the cavity partially covers the palm cooling object when the lid is covering the panel.

7. The palm cooling assembly of claim 1, further comprising an insulation material covering an interior surface of the housing and the lid.

8. The palm cooling assembly of claim 1, the temperature being between 30.0° Fahrenheit and 60.0° Fahrenheit.

9. The palm cooling assembly of claim 1, the refrigeration system further comprising:

an evaporator being positioned proximate to the panel within the interior area, the evaporator absorbing heat from the palm cooling object when the palm cooling object is positioned in the well, the evaporator being configured to heat a refrigerant whereby a phase of the refrigerant changes from a liquid to a vapor;

a condenser being positioned within the interior area, the condenser being spaced from the evaporator, the condenser being configured to cool the refrigerant whereby the phase of the refrigerant changes from the vapor to the liquid;

a compressor being fluidly coupled to the evaporator and to the condenser, the compressor being configured to increase a pressure of the refrigerant as the refrigerant moves through the compressor from the evaporator to the condenser; and an expansion device being fluidly coupled to the evaporator and to the condenser, the expansion device being configured to reduce the pressure of the refrigerant as the refrigerant moves through the expansion device from the condenser to the evaporator.

10. The palm cooling assembly of claim 9, wherein the peripheral wall has a vent extending therethrough, the vent being configured to discharge heat from the interior area, the heat being generated by the condenser, the vent being positioned proximate to the condenser.

11. The palm cooling assembly of claim 10, further comprising a grill being coupled to the peripheral wall and covering the vent.

12. The palm cooling assembly of claim 1, further comprising a central processing unit being positioned in the interior area, the central processing unit being operationally coupled with the refrigeration system, the central processing unit actuating the refrigeration system to control the temperature.

13. The palm cooling assembly of claim 12, further comprising a switch being coupled to the housing, the switch being operationally coupled with the central processing unit, the switch being actuatable to selectively turn the central processing unit off and on whereby the central processing unit actuates the refrigeration system to control the temperature of the interior area.

14. The palm cooling assembly of claim 12, further comprising a power source being electronically coupled with the central processing unit.

15. The palm cooling assembly of claim 14, the power source further comprising a rechargeable battery.

16. The palm cooling assembly of claim 14, further comprising a charging port being positioned inset into the peripheral wall and being exposed on the peripheral wall, the charging port being operationally coupled to the power source, the charging port being configured to receive a charging cord.

17. The palm cooling assembly of claim 1, wherein the lid is pivotably coupled to the peripheral wall.

18. The palm cooling assembly of claim 1, wherein the shape of the palm cooling object is spherical.

19. A palm cooling assembly comprising:

a housing having a base wall and a peripheral wall, the peripheral wall being attached to and extending upwardly from the base wall defining an interior area, the peripheral wall having an upper edge defining an opening into the interior area;

a panel being coupled to the upper edge and extending across the opening whereby the panel encloses the interior area, the panel comprising a thermally conductive material, the panel having a well therein;

a lid being positionable on the housing and abutting the upper edge to selectively cover the panel, the lid being pivotably coupled to the peripheral wall;

a handle being coupled to the lid;

a palm cooling object being removably positionable in the well, the palm cooling object being configured to inhibit conduction of heat away from the palm cooling object, the palm cooling object comprising a stainless-steel material, the palm cooling object being configured for gripping by a hand of a user, the palm cooling object having a shape being configured to at least partially cover a palm of the hand;

wherein the lid has a cavity therein, each of the well and the cavity having a shape being complementary to the shape of the palm cooling object, wherein the well partially covers the palm cooling object when the palm cooling object is positioned in the well and the cavity partially covers the palm cooling object when the lid is covering the panel;

an insulation material covering an interior surface of the housing and the lid;

a refrigeration system being positioned in the interior area, the refrigeration system being configured to control a temperature of the interior area whereby the palm cooling object is cooled to the temperature when the palm cooling object is positioned in the well, the temperature being between 30.0° Fahrenheit and 60.0° Fahrenheit, the refrigeration system comprising:

an evaporator being positioned proximate to the panel within the interior area, the evaporator absorbing heat from the palm cooling object when the palm cooling object is positioned in the well, the evaporator being configured to heat a refrigerant whereby a phase of the refrigerant changes from a liquid to a vapor;

a condenser being positioned within the interior area, the condenser being spaced from the evaporator, the condenser being configured to cool the refrigerant whereby the phase of the refrigerant changes from the vapor to the liquid;

a compressor being fluidly coupled to the evaporator and to the condenser, the compressor being configured to increase a pressure of the refrigerant as the refrigerant moves through the compressor from the evaporator to the condenser;

an expansion device being fluidly coupled to the evaporator and to the condenser, the expansion device being configured to reduce the pressure of the refrigerant as the refrigerant moves through the expansion device from the condenser to the evaporator;

a central processing unit being positioned in the interior area, the central processing unit being electronically coupled with the refrigeration system, the central processing unit actuating the refrigeration system to control the temperature;

a switch being coupled to the peripheral wall, the switch being electronically coupled with the central processing unit, the switch being actuatable to selectively turn the central processing unit off and on whereby the central processing unit actuates the refrigeration system to control the temperature of the interior area;

a power source being electronically coupled with the central processing unit, the power source being a rechargeable battery;

a charging port being positioned inset into the peripheral wall and being exposed on the peripheral wall, the charging port being electronically coupled to the power source, the charging port being configured to receive a charging cord;

the peripheral wall having a vent extending therethrough, the vent being configured to discharge heat from the interior area, the heat being generated by the power source and the condenser, the vent being positioned proximate to the power source and the condenser; and a grill being coupled to the peripheral wall and covering the vent.

* * * * *